(12) United States Patent
Ishida

(10) Patent No.: US 7,709,700 B2
(45) Date of Patent: May 4, 2010

(54) METHOD FOR IMPROVING PLANT TRANSFORMATION EFFICIENCY BY ADDING COPPER ION

(75) Inventor: Yuji Ishida, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 728 days.

(21) Appl. No.: 10/567,965

(22) PCT Filed: Aug. 12, 2004

(86) PCT No.: PCT/JP2004/011599

§ 371 (c)(1),
(2), (4) Date: Sep. 26, 2006

(87) PCT Pub. No.: WO2005/017152

PCT Pub. Date: Feb. 24, 2005

(65) Prior Publication Data

US 2007/0163007 A1 Jul. 12, 2007

(30) Foreign Application Priority Data

Aug. 13, 2003 (JP) .............................. 2003-293062

(51) Int. Cl.
*C12N 15/84* (2006.01)
*A01H 4/00* (2006.01)

(52) U.S. Cl. .................. 800/294; 800/320.1; 800/320.2; 435/424; 435/430.1; 435/431; 435/469

(58) Field of Classification Search .................. 800/294, 800/320.1, 320.2
See application file for complete search history.

(56) References Cited

U.S. PATENT DOCUMENTS

| | | | |
|---|---|---|---|
| 5,591,616 A | 1/1997 | Hiei et al. | |
| 6,162,965 A * | 12/2000 | Hansen | ........................ 800/278 |
| 6,235,529 B1 | 5/2001 | Lemaux et al. | |
| 6,329,571 B1 | 12/2001 | Hiei | |
| 6,541,257 B2 | 4/2003 | Lemaux et al. | |
| 6,900,057 B2 * | 5/2005 | Burns et al. | ............... 435/430.1 |
| 7,102,056 B1 * | 9/2006 | Lemaux et al. | .............. 800/278 |
| 7,238,862 B2 * | 7/2007 | Allison et al. | ................ 800/294 |
| 2001/0051610 A1 | 12/2001 | Bennett et al. | |
| 2004/0092473 A1 | 5/2004 | Xu et al. | |
| 2004/0092483 A1 | 5/2004 | Xu et al. | |
| 2004/0187177 A1 * | 9/2004 | Olhoft et al. | .................. 800/294 |

FOREIGN PATENT DOCUMENTS

| | | | |
|---|---|---|---|
| EP | 1 306 440 A1 | 5/2003 | |
| EP | 1 306 441 A1 | 5/2003 | |
| EP | 0 672 752 B1 | 5/2004 | |
| JP | 63-39595 A | 2/1988 | |
| JP | 2649287 B2 | 5/1997 | |
| JP | 2000-342253 A | 12/2000 | |
| JP | 2000-342255 A | 12/2000 | |
| JP | 2000-342256 A | 12/2000 | |
| JP | 3329819 B2 | 7/2002 | |
| JP | 2003-520253 A | 7/2003 | |
| JP | 2003-520253 A | 7/2003 | |
| KR | 2003-0045388 A | 6/2003 | |
| WO | WO-95/06722 A1 | 3/1995 | |
| WO | WO-99/16890 A2 | 8/1999 | |
| WO | WO-02/12520 A1 | 2/2002 | |
| WO | WO-03/018822 A1 | 3/2003 | |

OTHER PUBLICATIONS

Murashige & Skoog, 1962, Physiologia Plantarum, vol. 1, pp. 473-497.*
Paola Gori et al., Plant Cell Tissue Organ. Cult. (1998), vol. 53, No. 3, pp. 161 to 169.
Satoshi Tobita et al., Crop Science Society of Japan Kiji (1989), vol. 58, pp. 281 to 282.
Trifonova et al., "Agrobacterium-Mediated Transgene Delivery and Integration into Barley Under a Range of In Vitro Culture Conditions," Plant Science, vol. 161, pp. 871-880, 2001.
Yuan, "Role of Copper or Silver on Redifferentiation Frequency of Rice Callus," Hubei Agricultural Sciences, No. 1, pp. 17-19, 2003.
Zhu et al.,"Effect of Copper on Organ Differentiation in Plant", Plant Physiology Communications, vol. 35, No. 4, p. 333, 1999.
Grichko V.P. et al., J. Biotechnol. (2000), vol. 81, No. 1, pp. 45 to 53.
Emily Alexander et al., Appl. Environ. Microbiol. (1999), vol. 65, No. 8, pp. 3754 to 3756.
Grichko et al., Journal of Biotechnology, (2000), vol. 81, No. 1, pp. 45-63.
Alexander et al., Applied and Environmental Microbiology, (1999), vol. 65, No. 8, pp. 3754-3756.
Hiei et al., The Plant Journal, vol. 6, No. 2, pp. 271-282, (1994).
Ishida et al., Nature Biotechnology, vol. 14, pp. 745-750, (Jun. 1996).
Cheng et al., Plant Physiol, vol. 115, pp. 971-980, (1997).
Tingay et al. The Plant Journal, vol. 11, No. 6, pp. 1369-1376, (1997).
Zhao et al., Plant Molecular Biology, vol. 44, pp. 789-798, (2000).
Rogers et al., Methods for Plant Molecular Biology, pp. 423-436, CA: Academic Press Inc.

(Continued)

*Primary Examiner*—David T Fox
(74) *Attorney, Agent, or Firm*—Birch, Stewart, Kolasch & Birch, LLP

(57) ABSTRACT

The present invention provides a method for *Agrobacterium*-mediated gene introduction into a plant material, comprising:
1) treating the plant material, and then
2) infecting the plant material with an *Agrobacterium*, characterized in that a medium enriched in a metal salt containing copper ion is used in step 1) and/or 2). The present invention also provides a process for preparing a transformed plant characterized in that the gene introduction method of the present invention is used.

15 Claims, 5 Drawing Sheets

OTHER PUBLICATIONS

Visser R.G.F., Plant Tissue Culture Manual, B5: 1-9, (1991), Kluwer Academic Publishers.
McCormick, Plant Tissue Culture Manual, B5: 1-9, (1991), Kluwer Academic Publishers.
Lindsey et al., Plant Tissue Culture Manual, B7: 1-13, (1991), Kluwer Academic Publishers.
Potrykus et al., Agricultural Biotechnology, pp. 119-159, (1998), NY: Mercel Dekker Inc.
Negrotto et al., Plant Cell Reports, vol. 19, pp. 798-803, (2000).
Zhao et al., Molecular Breeding, vol. 8, pp. 323-333, (2001).
Frame et al., Plant Physiology, vol. 129, pp. 13-22, (2002).
Ishida et al., Plant Biotechnology, vol. 20, No. 1, pp. 57-66, (2003).
Ghaemi et al., Plant Cell, Tissue and Organ Culture, vol. 36, pp. 355-359, (1994).
Zhang et al., Plant Cell Reports, vol. 18, pp. 959-966, (1999).
Dahleen, Plant Cell, Tissue and Organ Culture, vol. 43 pp. 267-269, (1995).
Cho et al., Plant Science, vol. 138, pp. 229-244, (1998).
Sahrawat et al., J. Plant Physiol, vol. 154, pp. 517-522, (1999).
Trick et al., Transgenic Research, vol. 6, pp. 329-336, (1997).
Amoah et al., Journal of Experimental Botany, vol. 52, pp. 1135-1142, (May 2001).
Hoekema et al., Nature, vol. 303, p. 179-180, (May 1983).
Komari et al., Methods of Genetic Transformation: *Agrobacterium tumefaciens*, In I.K. Vasil (ed.), Molecular Improvement of Cereal Crops, Kluwer Academic Publishers, Dordrecht, pp. 43-82, (1999).
Li, et al., Genetic Trans. of Cassava, Nature Biotechnology, vol. 14, No. 6, pp. 736-740, XP002036203, 1996.
Purnhauser et al., "Effect of Copper on Shoot Regeneration in Wheat, Triticale, Rape and Tobacco Tissue Culture", Plant Cell, Tissue and Organ Culture, vol. 35, No. 2, pp. 131-139, XP008037427, 1993.
Purnhauser, L., "Stimulation of Shoot and Root Regeneration in Wheat *Triticum aestivum* Callus Cultures by Copper," Cereal Research Communications, vol. 19, No. 4, 1991, pp, 419-423, XP008037420.
Extended European Search Report dated Jun. 29, 2009 for corresponding European Application No. 09155496.4.

* cited by examiner

[Figure 1]
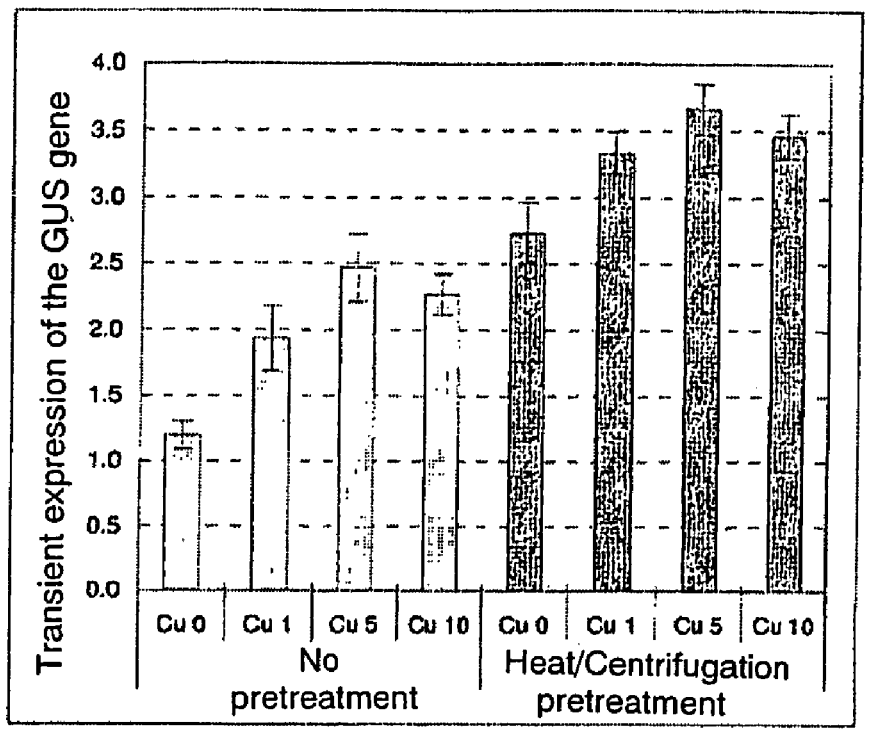
[Figure 2]
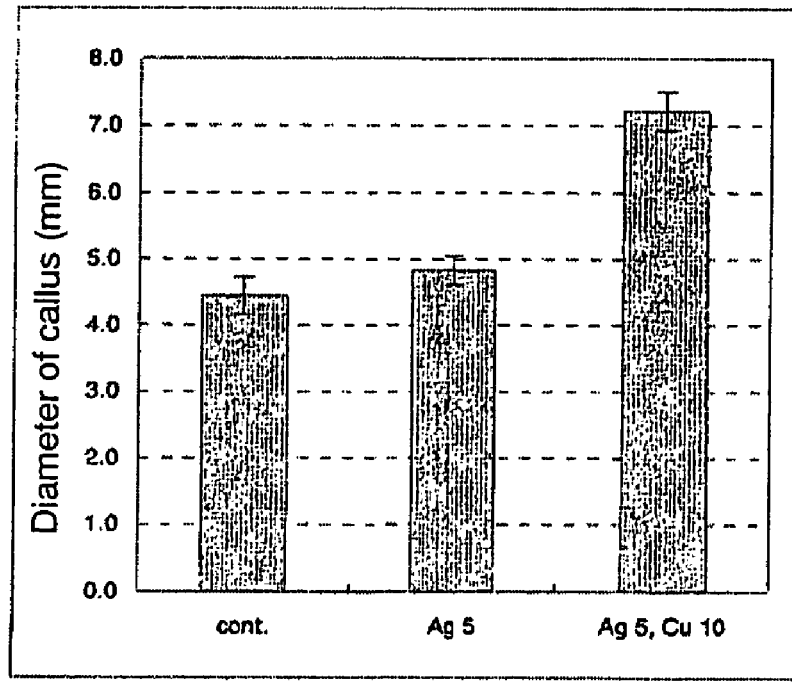

[Figure 3]
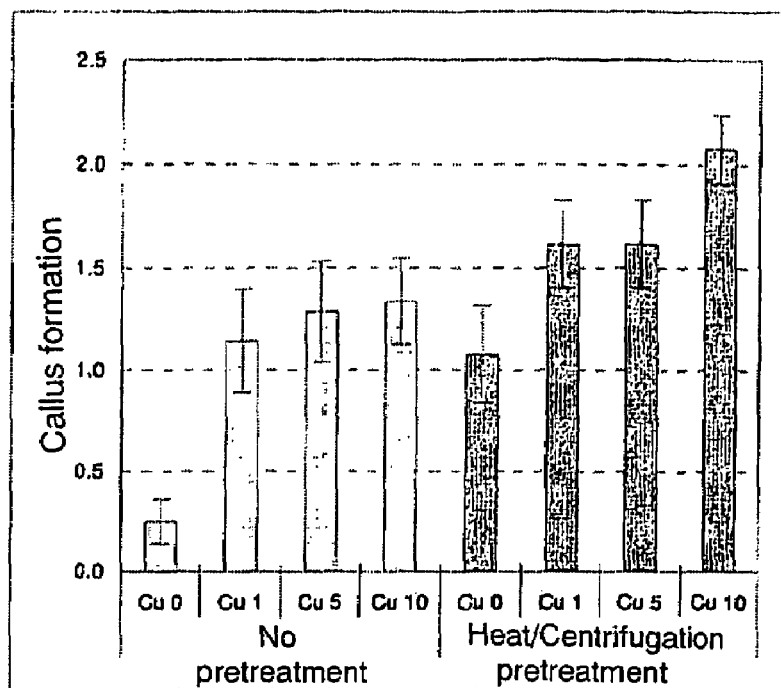
[Figure 4]
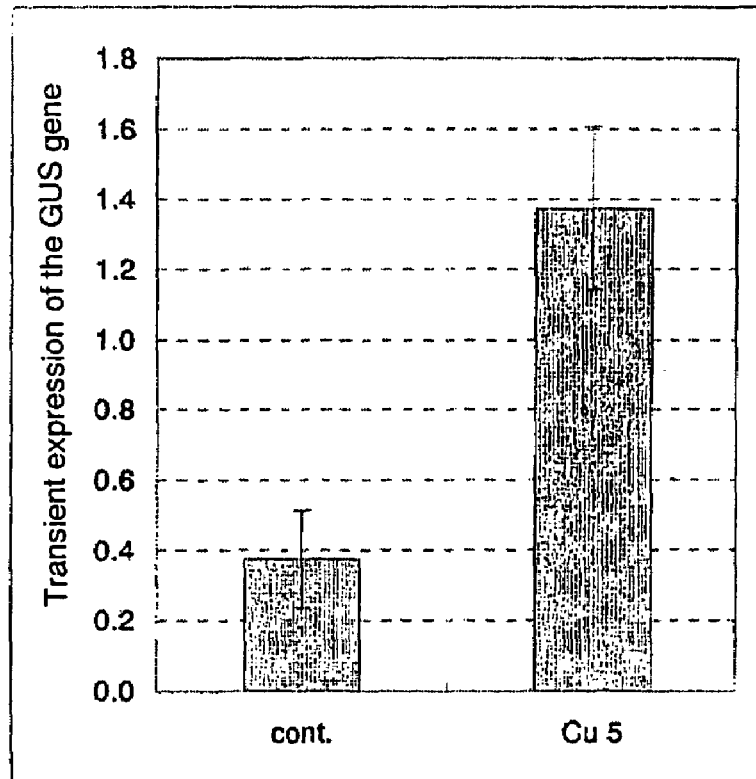

[Figure 5]
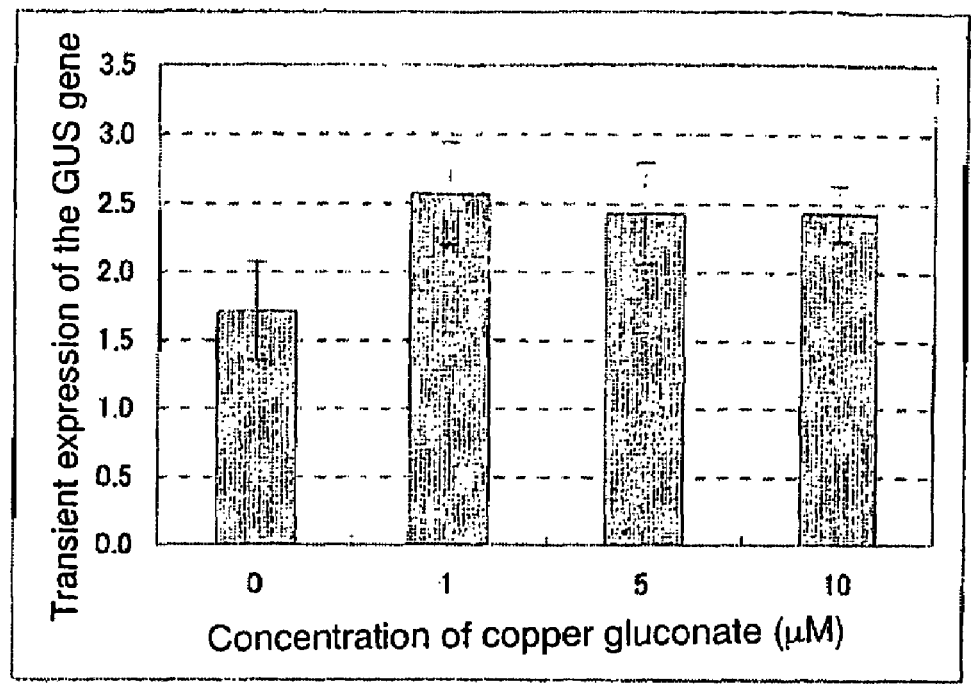
[Figure 6]
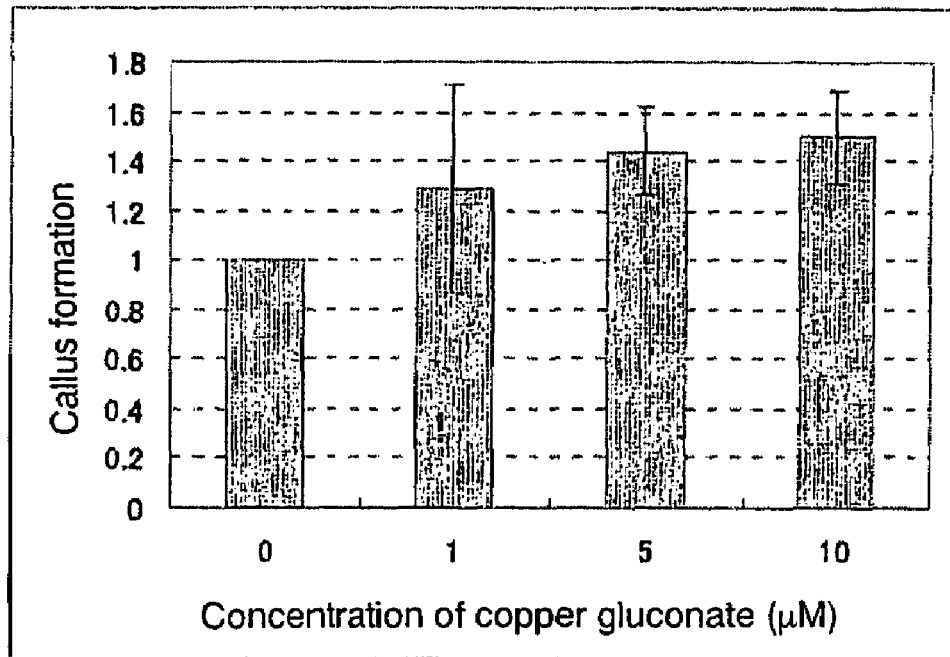

[Figure 7]
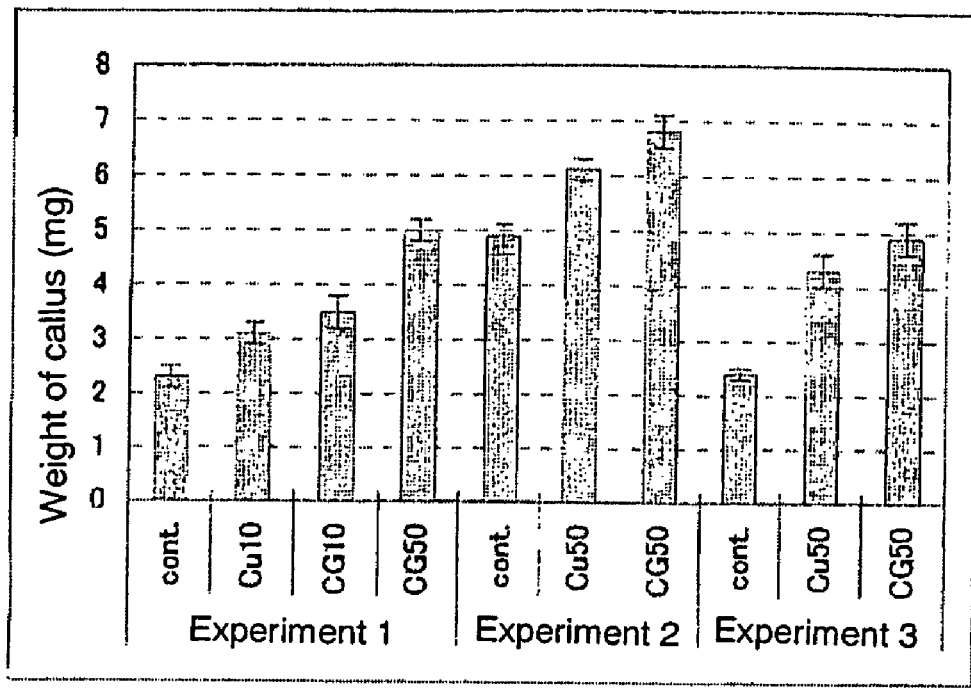
[Figure 8]
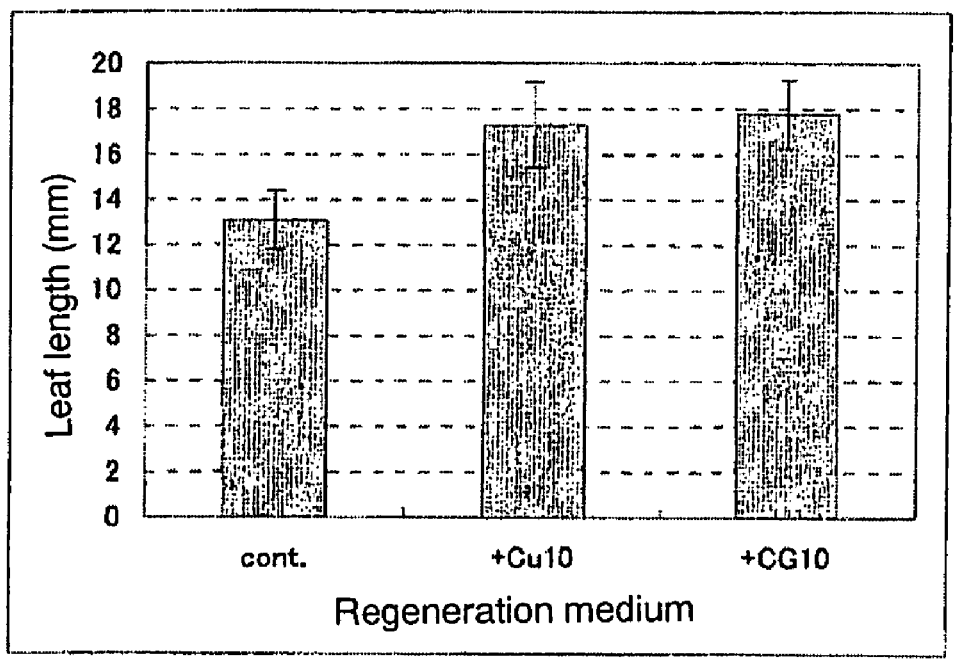

[Figure 9]
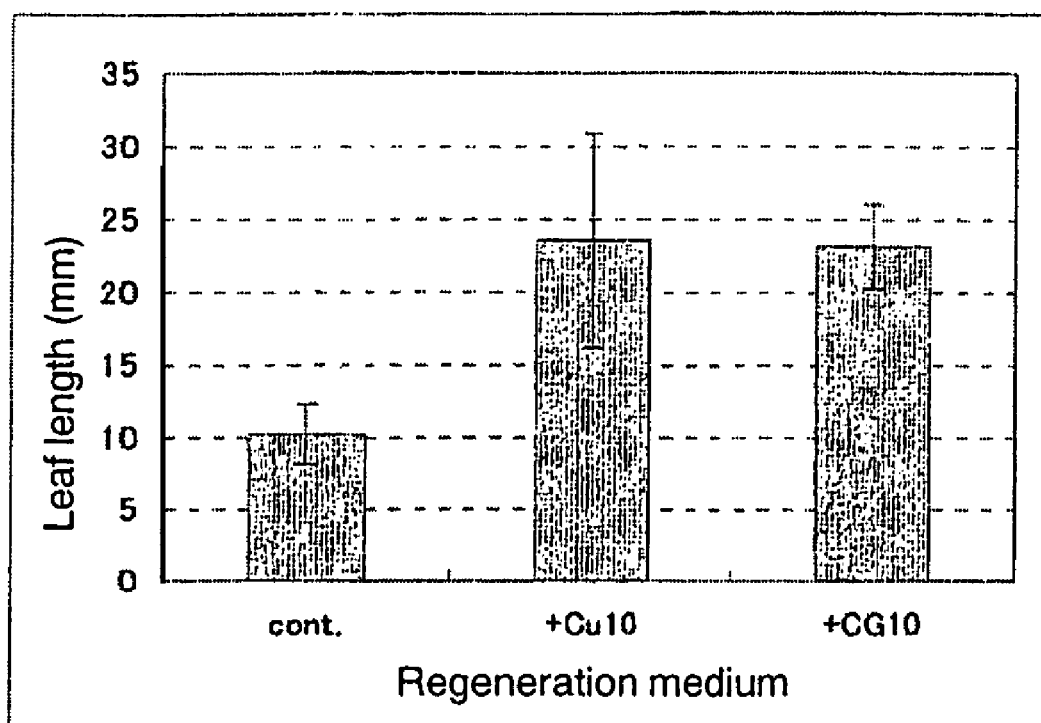

US 7,709,700 B2

METHOD FOR IMPROVING PLANT TRANSFORMATION EFFICIENCY BY ADDING COPPER ION

This application is a national stage application under 35 U.S.C. §371 of PCT International Application No. PCT/JP2004/011599 filed on Aug. 12, 2004, which claims the benefit of priority of Japanese Application Number 2003-293062 filed Aug. 13, 2003.

TECHNICAL FIELD

The present invention relates to an efficient method for *Agrobacterium*-mediated gene introduction into plant materials.

BACKGROUND ART

*Agrobacterium*-mediated gene introduction is a method for transforming plants through the use of a function of *Agrobacterium*. A soil bacterium *Agrobacterium* (*Agrobacterium tumefaciens*) functions in such a manner that the T-DNA forming a part of its Ti (tumor-inducing) plasmid involved in the pathogenicity of the *Agrobacterium* is integrated into the genome of a plant when it infects the plant. *Agrobacterium*-mediated plant transformation is a method for introducing a desired gene into the genome of a plant through the use of the function of *Agrobacterium* described above by constructing a transforming plasmid in which the T-DNA region of the Ti plasmid is replaced by the gene desired to be introduced into the plant genome and then using *Agrobacterium* prepared to carry the transforming plasmid in place of the Ti plasmid.

*Agrobacterium*-mediated plant transformation was originally developed mainly as a method for transforming dicotyledons because *Agrobacterium* were thought to infect only dicotyledons but not monocotyledons. Subsequently, various attempts for *Agrobacterium*-mediated gene introduction into monocotyledons were also made, and super-binary vectors having a part of the virulent genes of super-virulent *Agrobacterium* strains were developed and reported to be useful for stably transforming even monocotyledons such as rice and maize with relatively high efficiency (e.g., see Japanese Patent No. 2,649,287; Japanese Patent No. 3,329,819; Hiei, Y., et al., (1994), The Plant Journal, Vol. 6, p. 271-282; and Ishida, Y., et al., (1996), Nature Biotechnology, Vol. 4, p. 745-750). Successful examples of *Agrobacterium*-mediated transformation of monocotyledons such as wheat, barley and sorghum were also reported (e.g., see Cheng, M., et al., (1997), Plant Physiol., Vol. 115, p. 971-980; Tingay, S., et al., (1997), Plant J., Vol. 11, p. 1369-1376; and Zhao, Z-Y., et al., (2000), Plant Mol. Biol., Vol. 44, p. 789-798), and *Agrobacterium*-mediated transformation also began to be widely applied to monocotyledons.

*Agrobacterium*-mediated transformation generally has many advantageous features such as high efficiency, low copy number transgenes, transducibility of such a specific region as T-DNA without being fragmented, and short-term culture for obtaining transformants resulting in less mutation during culture. Thus, it is now widely used as the most useful means for transforming many plant species irrespective of whether they are dicotyledonous or monocotyledonous.

*Agrobacterium*-mediated transformation is equally performed in all plants by contacting a material tissue with an *Agrobacterium* suspension, coculturing them and then selecting a transformed cell to produce a transformed plant, though the materials and the compositions of the culture media vary with plant species. Generally, the plant tissue used as a material is infected with *Agrobacterium* without any special treatment except for optional sterilization (e.g., see Rogers, S. G., et al., (1988), Method for Plant Molecular Biology, p. 423-436, CA: Academic Press Inc.; Visser, R. G. F., (1991), Plant Tissue Culture Manual, B5:1-9, Kluwer Academic Publishers; McCormick, S., (1991), Plant Tissue Culture Manual, B6:1-9, Kluwer Academic Publishers; and Lindsey, K., et al., (1991), Plant Tissue Culture Manual, B7:1-13, Kluwer Academic Publishers).

*Agrobacterium*-mediated transformation has been reported for many plant species, but has the disadvantage that the transformation efficiency widely varies with plant species, genotypes and material tissues (e.g., see Potrykus, I., et al., (1998), Agricultural Biotechnology, NY: Mercel Dekker Inc., p. 119-159). It is important to develop a technology enabling transformed plants to be stably obtained with high efficiency throughout the year because many transformed plants must be produced when a cultivar containing a practical gene is to be bred. Moreover, transformation methods independent of plant species and genotypes would be very useful for efficiently breeding practical cultivars. Development of transformation methods independent of material plant tissues would also be required for efficient transformation.

Thus, it is important to develop a method capable of improving gene transduction efficiency or transforming even plant species or genotypes involving difficulty in gene transduction. Many techniques for efficiently obtaining transformed plants have already been reported in various aspects such as the adaptation of the compositions of culture media, the alteration of marker genes, or promoters or the investigation of materials and treatment methods for materials. For example, treatment methods for materials by injuring tissues to improve infection efficiency or by centrifuging (e.g., see International Publication No. WO02/12520; Japanese Patent Public Disclosure No. 2000-342256) or heating (e.g., see Japanese Patent Public Disclosure No. 2000-342255; Japanese Patent Public Disclosure No. 2000-342253) plant tissues without injuring them have been reported. The present inventors previously found that pressurization of plant tissues is useful for improving gene transduction efficiency (with the results unpublished).

Among monocotyledons, maize had the disadvantage that the *Agrobacterium*-mediated transformation efficiency is lower than that of rice. Various attempts have already been made to improve the *Agrobacterium*-mediated transformation efficiency of maize (e.g., see Negrotto, D., et al., (2000), Plant Cell Reports, Vol. 19, p. 798-803; Zhao, Z-Y., et al., (2001), Mol. Breed., Vol. 8, p. 323-333; Frame, B. R., et al., (2002), Plant Physiol., Vol. 129, p. 13-22; and , Ishida, Y., et al., (2003), Plant Biotechnology, Vol. 14, p. 57-66). Various previous attempts to improve the *Agrobacterium*-mediated transformation efficiency of maize include selecting transformed cells on N6 basal medium (e.g., see Zhao, Z-Y., et al., (2001), Mol. Breed., Vol. 8, p. 323-333), adding silver nitrate and carbenicillin to culture media (e.g., see Zhao, Z-Y., et al., (2001), Mol. Breed., Vol. 8, p. 323-333; and , Ishida, Y., et al., (2003), Plant Biotechnology, Vol. 14, p. 57-66), adding cysteine to coculture media (e.g., see Frame, B. R., et al., (2002), Plant Physiol., Vol. 129, p. 13-22), etc., but the resulting effects are still low. Transformation methods with higher transformation efficiency would be desirable especially for major crops associated with low transformation efficiency such as maize not only when practical transformed plants are to be produced but also when the effect of a novel gene is to be tested.

Copper sulfate is contained as a minor salt in a wide variety of media. Normally, the concentration of copper sulfate in plant tissue culture media is 0.1 µM. Recent report shows that various effects were observed when adding copper sulfate at 50-fold to 500-fold higher concentrations than normal levels to media in tissue cultures and transformation tests of monocotyledons. Ghaemi et al. (see Ghaemi, M., et al., (1994), Plant Cell, Tissue and Organ Culture, Vol. 36, p. 355-359) reported that embryoid formation increases by culturing anthers of wheat in a medium containing 10 mg/l copper sulfate and 2.5-5 mg/l silver nitrate. Zhang et al. (see Zhang, S., et al., (1999), Plant Cell Reports, Vol. 18, p. 959-966) reported that the induction ratio of shoot meristematic cultures (SMCs) increases by culturing shoots having emerged from ripe seeds of barley in a medium containing 5 µM copper sulfate and 30 g/l maltose. They describe that maltose is effective for decreasing brown tissue and that copper sulfate is effective for promoting shoot growth when shoot meristematic cultures are induced. It was also reported that the regeneration ratio or the number of regenerated plants per callus increases in calli obtained by culturing immature embryos of barley (e.g., see Dahleen, L. S., (1995), Plant Cell, Tissue and Organ Culture, Vol. 43, p. 267-269; and, Cho, M-J., et al., (1998), Plant Science, Vol. 138, p. 229-244) and rice (e.g., see Sahrawat, A. K. and Chand, S., (1999), J. Plant Physiol., Vol. 154, p. 517-522) in media containing copper sulfate. It was also reported that green tissues having regeneration potential induced in media containing copper sulfate are suitable as materials for transformation (e.g., see Visser, R. G. F., (1991), Plant Tissue Culture Manual, B5:1-9, Kluwer Academic Publishers; and, McCormick, S., (1991), Plant Tissue Culture Manual, B6:1-9, Kluwer Academic Publishers).

Ishida et al. (see Ishida, Y., et al., (2003), Plant Biotechnology, Vol. 20, p. 57-66) investigated callus formation from immature embryos by culturing immature embryos of maize (cultivar: H99) inoculated and co-cultured with Agrobacterium, on media containing 1-100 µM copper sulfate. The callus formation improved in media containing 1-10 µM copper sulfate, but slightly.

As described above, previous reports showed that various effects were observed in tissue cultures of monocotyledons by adding high concentrations of copper sulfate to media. However, there has been no report on the effects of adding a metal salt containing copper ion on gene introduction efficiency and/or transformation efficiency.

REFERENCES

Patent document 1: Japanese Patent No. 2,649,287.
Patent document 2: Japanese Patent No. 3,329,819.
Patent document 3: International Publication No. WO 02/12520.
Patent document 4: Japanese Patent Public Disclosure No. 2000-342256.
Patent document 5: Japanese Patent Public Disclosure No. 2000-342255.
Patent document 6: Japanese Patent Public Disclosure No. 2000-342253.
Patent document 7: U.S. Pat. No. 6,235,529.
Patent document 8: U.S. Pat. No. 6,541,257.
Patent document 9: International Publication No. WO 95/06722.
Non-patent document 1: Hiei, Y., et al., (1994), The Plant Journal, Vol. 6, p. 271-282.
Non-patent document 2: Ishida, Y., et al., (1996), Nature Biotechnology, Vol. 4, p. 745-750.
Non-patent document 3: Cheng, M., et al., (1997), Plant Physiol., Vol. 115, p. 971-980.
Non-patent document 4: Tingay, S., et al., (1997), Plant J., Vol. 11, p. 1369-1376.
Non-patent document 5: Zhao, Z-Y., et al., (2000), Plant Mol. Biol., Vol. 44, p. 789-798.
Non-patent document 6: Rogers, S. G., et al., (1988), Method for Plant Molecular Biology, p. 423-436, CA: Academic Press Inc.
Non-patent document 7: Visser, R. G. F., (1991), Plant Tissue Culture Manual, B5:1-9, Kluwer Academic Publishers.
Non-patent document 8: McCormick, S., (1991), Plant Tissue Culture Manual, B6:1-9, Kluwer Academic Publishers.
Non-patent document 9: Lindsey, K., et al., (1991), Plant Tissue Culture Manual, B7:1-13, Kluwer Academic Publishers.
Non-patent document 10: Potrykus, I., et al., (1998), Agricultural Biotechnology, NY: Mercel Dekker Inc., p. 119-159.
Non-patent document 11: Negrotto, D., et al., (2000), Plant Cell Reports, Vol. 19, p. 798-803.
Non-patent document 12: Zhao, Z-Y., et al., (2001), Mol. Breed., Vol. 8, p. 323-333.
Non-patent document 13: Frame, B. R., et al., (2002), Plant Physiol., Vol. 129, p. 13-22.
Non-patent document 14: Ishida, Y., et al., (2003), Plant Biotechnology, Vol. 14, p. 57-66.
Non-patent document 15: Ghaemi, M., et al., (1994), Plant Cell, Tissue and Organ Culture, Vol. 36, p. 355-359.
Non-patent document 16: Zhang, S., et al., (1999), Plant Cell Reports, Vol. 18, p. 959-966.
Non-patent document 17: Dahleen, L. S., (1995), Plant Cell, Tissue and Organ Culture, Vol. 43, p. 267-269.
Non-patent document 18: Cho, M-J., et al., (1998), Plant Science, Vol. 138, p. 229-244.
Non-patent document 19: Sahrawat, A. K. and Chand, S., (1999), J. Plant Physiol., Vol. 154, p. 517-522.
Non-patent document 20: Trick, H. N. and Finer, J. J., (1997), Transgenic Research, Vol. 6, p. 329-336.
Non-patent document 21: Amoah, B., et al., (2001), Journal of Experimental Botany, Vol. 52, P. 1135-1142.
Non-patent document 22: Hoekema, A., et al., (1983), Nature, Vol. 303, p. 179-180.
Non-patent document 23: Komari, T. and Kubo T., (1999), Methods of Genetic Transformation: *Agrobacterium tumefaciens*. In Vasil, I. K. (ed.) Molecular improvement of cereal crops., Kluwer Academic Publishers, Dordrecht, p. 43-82.

DISCLOSURE OF THE INVENTION

Problems to be Solved by the Invention

An object of the present invention is to develop a method by which gene introduction is achieved with higher gene introduction efficiency than obtained by conventional methods for *Agrobacterium*-mediated gene introduction into plants. Another object of the present invention is to develop a method by which transformed cells are grown with higher growth efficiency than obtained from plant tissues by conventional methods for *Agrobacterium*-mediated gene introduction into plants. Still another object of the present invention is to develop a process for preparing a transformed plant using any of these methods.

Means for Solving the Problems

As a result of careful studies to attain the objects described above, the present inventors found that stable and highly efficient gene introduction is achieved and stable and highly efficient cell growth is observed from the gene-introduced tissues by *Agrobacterium*-mediated gene introduction into plants using a medium enriched in a metal salt as compared with cases where a medium containing the metal salt at a normal level is used. The present inventors also found that stable and more highly efficient gene introduction is achieved by heating/centrifuging plant materials before they are infected with *Agrobacterium* in addition to gene introduction using a medium enriched in a metal salt. The present inventors also found that plant materials which gene introduction is carried out by using a medium enriched in a metal salt dramatically improve transformation efficiency by selecting transformed cells from the gene-introduced plant materials as compared with cases where a medium containing the metal salt at a normal level is used.

Accordingly, the present invention relates to a method for *Agrobacterium*-mediated gene introduction into a plant material, comprising:

1) treating the plant material, and 2) infecting the plant material with an *Agrobacterium*, characterized in that a medium enriched in a metal salt containing copper ion is used in step 1) and/or 2).

In the method of the present invention, the metal salt present at a high concentration in the medium is a metal salt containing copper ion. A preferred metal salt used in the present invention is copper sulfate or copper gluconate, most preferably copper sulfate. Copper sulfate is not limited to either anhydrous or hydrated salt.

In the method of the present invention, the medium enriched in a metal salt means a medium containing a metal salt at a high concentration relative to the concentrations of the metal salt in basal media well known to those skilled in the art such as N6 basal medium, MS (LS) basal medium, B5 basal medium, NN basal medium, NT basal medium, Kao's basal medium, White's basal medium, etc. The high concentration means a concentration higher than the concentrations of the metal salt in the basal media.

Specifically, a medium prepared on the basis of a basal medium such as N6 basal medium containing 0 mg/l, MS (LS) basal medium containing 0.025 mg/l, B5 basal medium containing 0.025 mg/l, NN basal medium containing 0.025 mg/l, NT basal medium containing 0.025 mg/l, Kao's basal medium containing 0.025 mg/l, or White's basal medium containing 0 mg/l $CuSO_4.5H_2O$ and containing a higher concentration of copper sulfate than the copper sulfate concentration of the basal medium is a medium enriched in a metal salt.

As used herein, the metal salt containing copper ion means a metal salt containing copper ion normally absent or contained in minor amounts in the basal media listed above.

Examples of preferred concentrations are 1-100 μM, preferably 1-50 μM, more preferably 1-10 μM copper sulfate and copper gluconate.

In the method of the present invention, the step in which a medium enriched in a metal salt is used is any one of step 1) of preparing the plant material, and/or step 2) of infecting the plant material with an *Agrobacterium*. Preferably, a medium enriched in a metal salt is used in at least step 2) of infecting the plant material with an *Agrobacterium*. More preferably, a medium enriched in a metal salt is used during at least the co-culture stage included in step 2) of infecting the plant material with an *Agrobacterium*.

The method of the present invention may further comprise subjecting the plant material to at least one treatment selected from the group consisting of pressurization, heat treatment, centrifugation and sonication in step 1) of preparing the plant material and/or step 2) of infecting the plant material with an *Agrobacterium*. Pressurization of the plant material is performed in liquid media at 1.7-10 atm for 0.1 second to 4 hours, preferably 2.4-8 atm for 1 second to 30 minutes. Heat treatment of the plant material can be performed by the methods described in various documents (Japanese Patent Public Disclosure No. 2000-342255; and Japanese Patent Public Disclosure No. 2000-342253), e.g., at 33-60° C. for 5 seconds to 24 hours, preferably 46° C. for 3 minutes. Centrifugation of the plant material can be performed by the method of Hiei et al. (International Publication No. WO02/12520; and Japanese Patent Public Disclosure No. 2000-342256), e.g., at 100 G -250,000 G for 1 second to 4 hours, preferably 20,000 G for 10 minutes. Sonication can be performed by the methods described in documents (e.g., Trick, H. N. and Finer, J. J., (1997), Transgenic Research, Vol. 6, p. 329-336; and Amoah, B., et al., (2001), Journal of Experimental Botany, Vol. 52, p. 1135-1142). Any one of these treatments such as pressurization, heat treatment, centrifugation and sonication may be performed or any combination may be performed.

The method of the present invention may further comprise the steps of:

3) selecting a transformed cell, and 4) optionally regenerating the selected transformant, subsequent to step 2) of infecting the plant material with an *Agrobacterium*.

The method of the present invention may further comprise the steps of:

3) selecting a transformed cell, and 4) optionally regenerating the selected transformant, subsequent to step 2) of infecting the plant material with an *Agrobacterium*, wherein a medium enriched in a metal salt containing copper ion is used in at least one of the steps above.

The gene introduction method of the present invention improves gene introduction efficiency as well as transformation efficiency, with the result that transformed plants can be efficiently obtained. Thus, the present invention also relates to a process for preparing a transformed plant characterized in that a gene introduction method of the present invention is used.

The present inventors also found that the growth of regenerated plants is promoted by regenerating transformed plant materials using a medium enriched in a metal salt containing copper ion as compared with cases where a medium containing the metal salt containing copper ion at a normal level is used.

Thus, the present invention also relates to a process for preparing a transformed plant by *Agrobacterium*-mediated transformation of a plant material, comprising:

1) preparing a plant material, 2) infecting the plant material with an *Agrobacterium*, 3) selecting a transformed cell, and 4) regenerating the selected transformant, characterized in that a medium enriched in a metal salt containing copper ion is used in step 4).

Alternatively, the present invention relates to a method for promoting the growth of a regenerated plant characterized in that a medium enriched in a metal salt containing copper ion is used in the step of regenerating a plant from a dedifferentiated plant cell. The regenerated plant cell here may or may not be a transformed cell, and when it is a transformed cell, it may or may not be transformed by an *Agrobacterium*-mediated method.

Methods for *Agrobacterium*-Mediated Gene Introduction and Transformation

*Agrobacterium*-mediated gene introduction typically comprises the steps of:

a) preparing a plant material;

b) preparing an *Agrobacterium* carrying a vector containing a desired transgene; and c) infecting the plant material prepared in step a) with the *Agrobacterium* prepared in step b).

In order to obtain a transformant, step c) may be further followed by the steps of:

d) selecting a transformed cell; and e) optionally regenerating the selected transformant.

Specifically, for monocotyledons, it is possible to use a method characterized in that the plant material is cultured in a medium containing auxin (e.g., 2,4-D (2,4-dichlorophenoxyacetic acid)) or cytokinin or the like to turn it into a dedifferentiated state or a state under dedifferentiation in step a) and infected with *Agrobacterium* in step c) as described in a document (Japanese Patent No. 2,649,287); or a method characterized in that an immature embryo of the plant is used as the plant material and cultured in a medium containing auxin (e.g., 2,4-D) or cytokinin or the like in step c) without dedifferentiating it in step a) as described in a document (Japanese Patent No. 3,329,819).

Step a)

The "plant" used herein for gene introduction means to include both monocotyledons and dicotyledons. Monocotyledons include, but are not limited to, rice, maize, barley, wheat, asparagus, sorghum and the like. Dicotyledons include, but not limited to, tobacco, soybean, potato, cotton, sunflower and the like. Preferably, the plant is a monocotyledon, most preferably maize.

The "plant material" encompasses all the aspects of plants to be used for *Agrobacterium*-mediated transformation of plants including, but not limited to, plant cells, leaves, roots, stems, fruits, plant tissues of any other parts, immature embryos, calli or adventitious embryo-like tissues (hereinafter referred to as calli or the like, or simply calli), or whole plants.

A desirable plant form used in the methods of the present invention is an immature embryo or a callus, most desirably an immature embryo. As used herein, the expressions of plant cell, tissue and whole plant have the same meanings as commonly used in the art. As used herein, the immature embryo means the embryo of an immature seed under maturation after pollination. The stage (maturation phase) of the immature embryo used in the methods of the present invention are not specifically limited, and it may be collected at any stage after pollination. However, it is preferably at a post-pollination stage of two days or more. Preferably, the scutellum of an immature embryo capable of inducing a callus that can be dedifferentiated to regenerate a normal plant by the method described below after the transformation described below is used. The immature embryo is preferably an immature embryo of an inbred line, F1 between inbred lines, F1 between an inbred line and an open-pollinated cultivar, or a commercially available F1 cultivar. As used herein, a callus means an undifferentiated cell clump under uncontrolled growth. A callus can be obtained by culturing a differentiated cell of a plant tissue in a medium containing a plant growth regulator such as auxin (e.g., 2,4-D) or cytokinin (referred to as dedifferentiation medium). The treatment for obtaining a callus is called dedifferentiation treatment and this process is called dedifferentiation process.

In step a), a material suitable for transformation is prepared by extracting a plant tissue, immature embryo or the like as appropriate from a plant, seed or the like. Optionally, the plant material may be cultured before it is infected with an *Agrobacterium*.

The present invention is characterized in that a medium enriched in a metal salt containing copper ion is used during the process of preparing a plant material in step a), and/or during the process of infecting the plant material with an *Agrobacterium* in step c). Additionally, pressurization may be performed during the process of preparing a plant material in step a).

Step b)

A soil bacterium *Agrobacterium* (*Agrobacterium tumefaciens*) has long been known to induce crown gall disease in many dicotyledons, and in 1970s, it was discovered that its Ti plasmid is involved in pathogenicity and that the T-DNA forming a part of the Ti plasmid is integrated into plant genomes. Subsequently, it was shown that the T-DNA contains genes involved in the synthesis of hormones necessary for inducing cancers (cytokinin and auxin) and that these genes are expressed in plants though they are bacterial genes. Excision of the T-DNA and its transfer to plants require genes existing in the virulence region (vir region) on the Ti plasmid, and excision of the T-DNA requires border sequences flanking the T-DNA. Another *Agrobacterium*, *Agrobacterium rhizogenes* has a similar system based on its Ri plasmid (e.g., FIGS. 3 and 4 of Japanese Patent Public Disclosure No. 2000-342256).

A desired gene was expected to be integrated into plant genomes by inserting it onto the T-DNA because the T-DNA is integrated into plant genomes by infection with *Agrobacterium*. However, it was difficult to insert a gene onto the T-DNA on the Ti plasmid by standard genetic engineering techniques because the Ti plasmid is as large as 190 kb or more. Thus, a method for inserting an exogenous gene onto the T-DNA was developed.

Initially, disarmed strains in which the hormone-synthesizing genes have been removed from the T-DNA of the tumor-inducing Ti plasmid such as LBA4404 (see Hoekema, A., et al., (1983), Nature, Vol. 303, p. 179-180), C58C1 (pGV3850), and GV3Ti11SE were prepared. Two methods were developed for introducing a desired gene into the T-DNA of the Ti plasmid of *Agrobacterium* or introducing the T-DNA carrying a desired gene into *Agrobacterium* using these strains. The first method is called the intermediate vector method wherein an intermediate vector that can be easily genetically manipulated to insert a desired gene and that can be replicated in *E. coli* is inserted into the T-DNA region of a disarmed Ti plasmid of *Agrobacterium* by homologous recombination via triparental mating.

The second method is called the binary vector method based on the finding that the vir region is required for integration of the T-DNA into plants but need not be present on the same plasmid to serve its functions. There exist virA, virB, virC, virD, virE and virG in the vir region (Dictionary of Plant Biotechnology, published by Enterprise (1989)), and the vir region refers to a region containing all of these virA, virB, virC, virD, virE and virG. Thus, a binary vector which is a small plasmid replicable in both *Agrobacterium* and *E. coli* into which the T-DNA is integrated, is introduced into *Agrobacterium* having a disarmed Ti plasmid.

Introduction of a binary vector into *Agrobacterium* can be performed by known methods such as electroporation and triparental mating. Binary vectors include pBIN19, pBI121, pGA482, etc., and many novel binary vectors based on them were constructed and used for transformation. In the Ri plasmid system, similar vectors were constructed and used for transformation.

*Agrobacterium* A281 is a super-virulent strain that has a wide host range and higher transformation efficiency than those of other strains. This characteristic is attributed to pTiBo542 of the Ti plasmid carried by A281. Two novel systems were developed using pTiBo542 until now. One uses EHA101 and EHA105 strains carrying a disarmed Ti plasmid of pTiBo542 and finds applications in transformation of various plants as a system having a high transforming ability by applying these strains to the binary vector system described above.

The other is a 'super-binary' vector (see Hiei, Y., et al., (1994), The Plant Journal, Vol. 6, p. 271-282; Ishida, Y., et al., (1996), Nature Biotechnology, Vol. 4, p. 745-750; Komari, T. and Kubo T., (1999), Methods of Genetic Transformation: *Agrobacterium tumefaciens*. In Vasil, I. K. (ed.) Molecular improvement of cereal crops., Kluwer Academic Publishers, Dordrecht, p. 43-82; and International Publication No. WO 95/06722) system (e.g., FIG. 4 of Japanese Patent Public Disclosure No. 2000-342256). This system is a kind of binary vector system because it consists of a disarmed Ti plasmid having the vir region (virA, virB, virC, virD, virE and virG (hereinafter sometimes each referred to as "vir fragment region")) and a plasmid having the T-DNA. However, it differs in that it uses a super-binary vector which a fragment of the vir region substantially deprived of at least one of the vir fragment regions (preferably the fragment including at least virB or virG, more preferably the fragment including virB and virG) is integrated, as the plasmid having the T-DNA, i.e. a binary vector. Homologous recombination via triparental mating can be used as a convenient method for introducing the T-DNA region containing a desired gene into *Agrobacterium* carrying a super-binary vector.

*Agrobacterium* that can be used as hosts in the methods of the present invention are not specifically limited, but preferably include *Agrobacterium tumefaciens* (e.g., *Agrobacterium tumefaciens* LBA4404 (see Hoekema, A., et al., (1983), Nature, Vol. 303, p. 179-180) and EHA101 as described above).

According to the methods of the present invention, significant effects can be obtained, without specific limitation, by using any gene transduction system based on the expression of the genes in the virulence (vir) region in *Agrobacterium*. Thus, benefits of the present invention can be obtained by using any vector system such as intermediate vectors, binary vectors, super-virulent binary vectors and super-binary vectors as described above. The same effects can also be obtained by using different vector systems obtained by modifying these vectors (e.g., by excising a part or all of the vir region of *Agrobacterium* and additionally inserting it into a plasmid, or excising a part or all of the vir region and introducing it as a part of a novel plasmid into *Agrobacterium*). According to the methods of the present invention, the infection efficiency can also be virtually improved with wild-type *Agrobacterium* by increasing the introduction efficiency of the wild-type T-DNA region into plants.

A desired gene to be introduced into plants can be inserted at a restriction endonuclease site in the T-DNA region of the plasmid described above according to standard procedures, and can be selected on the basis of a suitable selective marker such as a gene having resistance to a drug such as kanamycin or paromomycin simultaneously or separately inserted into the plasmid. A desired DNA may not be readily inserted into the T-DNA region of a large plasmid having many restriction endonuclease sites by conventional subcloning methods. In such cases, the desired DNA can be inserted by homologous recombination in cells of *Agrobacterium* via triparental mating. The size of the transgene is not limited, but preferably about 100 bp to 200 kbp.

Introduction of the plasmid into an *Agrobacterium* such as *Agrobacterium tumefaciens* can be accomplished by conventional methods such as triparental mating as described above, electroporation, electroinjection, and chemical treatments with PEG or the like.

The gene to be introduced into plants is basically located between the left and right border sequences flanking the T-DNA in the same manner as in conventional techniques. However, only one border sequence may exist because the plasmid is circular, or three or more border sequences may exist when multiple genes are to be located at different sites. The gene may also be located on the Ti or Ri plasmid or on another plasmid in *Agrobacterium*. Alternatively, it may also be located on multiple types of plasmids.

Step c)

*Agrobacterium*-mediated gene introduction can be performed simply by contacting a plant material with an *Agrobacterium*. For example, it can be performed by preparing an *Agrobacterium* suspension having a cell density of about $10^6$ to $10^{11}$ cells/ml, immersing a plant material in this suspension for about 3 to 10 minutes, and then co-culturing them on a solid medium for several days.

Preferably, the plant material is co-cultured with *Agrobacterium* at the same time the plant material is infected with *Agrobacterium* or before *Agrobacterium* is removed after infection. Known media can be used for co-culture. For example, LS-AS medium and nN6-As medium used in the examples below or other media such as N6S3-AS medium and 2N6-AS medium (see Hiei, Y., et al., (1994), The Plant Journal, Vol. 6, p. 271-282) are known.

In the present invention, the plant material may be subjected to at least one treatment selected from the group consisting of pressurization, heat treatment, centrifugation and sonication before or during step c) of infecting the plant material with an *Agrobacterium*. These treatments are also known to increase gene transduction efficiency in *Agrobacterium*-mediated gene transduction into plant materials. For example, centrifugation is described in documents (e.g., International Publication No. WO 02/12520; and Japanese Patent Public Disclosure No. 2000-342256), and preferably performed at 100 G to 250,000 G for 1 second to 4 hours. Heat treatment is described in documents (e.g., Japanese Patent Public Disclosure No. 2000-342255), and preferably performed in a temperature range of 33° C. to 60° C. for 5 seconds to 24 hours. Sonication is described in documents (e.g., Trick, H. N. and Finer, J. J., (1997), Transgenic Research, Vol. 6, p. 329-336; and Amoah, B., et al., (2001), Journal of Experimental Botany, Vol. 52, p. 1135-1142).

Any one of these treatments such as pressurization, heating, centrifugation and sonication may be performed or any combination may be performed. For example, Rogers, S. G., et al., (1988), Method for Plant Molecular Biology, p. 423-436, CA: Academic Press Inc. describes a combination of heat treatment and centrifugation.

Steps d) and e)

In order to obtain a transformant if desired, step c) described above should be followed by the steps of:

d) selecting a transformed cell; and e) optionally regenerating the selected transformant. That is, in order to perform transformation of a plant, it is typically necessary to select a plant cell containing an exogenous gene stably integrated into the chromosome after the exogenous gene is introduced into the plant cell.

In the present invention, a medium enriched in a metal salt containing copper ion may be used in step d) of selecting a transformed cell, and/or step e) of optionally regenerating the selected transformant.

The step of selecting a transformed cell means selecting a cell having a desired trait based on phenotype data and/or physical data.

Phenotype data such as transformation efficiency can be obtained by evaluating the expression of a marker gene and/or a selective marker gene co-introduced with a gene desired to be introduced into a plant. Marker genes and/or selective marker genes that can be used include e.g., the GUS (β-glucuronidase) gene, antibiotic resistance genes (e.g., PPT (phosphinothricin) resistance genes, kanamycin resistance genes)), etc. When the GUS gene is used as a marker gene, transformation efficiency can be evaluated from the coloration resulting from the cleavage of X-gulc (5-bromo-4-chloro-3-indolyl-β-D-glucuronic acid) by GUS. When a gene resistant to an antibiotic is used as a selective marker gene, evaluation can be made from the extent of growth on a selective medium containing the antibiotic after transformation.

To ascertain that the exogenous gene has been stably integrated into the chromosome, physical data such as southern blotting may be obtained. The selecting step may also be performed based on transmission to progeny via sexual reproduction and genetic and molecular analyses in progeny populations.

Optionally, the selected transformant may be regenerated and the regenerated plant may be grown to a whole plant. Regeneration from the selected transformant to a whole plant can be performed by known methods (e.g., Hiei, Y., et al., (1994), The Plant Journal, Vol. 6, p. 271-282; and Ishida, Y., et al., (1996), Nature Biotechnology, Vol. 4, p. 745-750).

The methods of the present invention improve gene introduction efficiency and/or transformation efficiency and/or promote the growth of regenerated plants as compared with cases where a medium containing a metal salt at a normal level is used. Gene introduction efficiency can be evaluated by e.g., assessing the area of the transient expression of the transgene. In the examples below, the transient expression of the GUS gene in the scutella of immature embryos was evaluated on a scale of five ratings from 1 (occasional spot expression) to 5 (expression on the entire surface of the scutellum). Alternatively, it can also be evaluated by counting the total number of spots in cases where the total expression level is low.

Transformation efficiency can be calculated by e.g., counting the number of regenerated plants expressing the GUS gene as transformants among those obtained from inoculated immature embryos and dividing the total number by the number of inoculated immature embryos. Alternatively, it can also be calculated by counting the number of regenerated plants showing resistance against a selective pressure as transformants and dividing the total number by the number of inoculated immature embryos.

The promotion of the growth of regenerated plants can be evaluated by e.g., comparing the leaf length, leaf area, and/or weight of regenerated plants obtained on a medium enriched in a metal salt and a medium containing the metal salt at a normal level.

The following examples further illustrate the present invention without, however, limiting the invention thereto. Those skilled in the art can readily add modifications/changes to the present invention on the basis of the description herein, and such modifications/changes are included in the technical scope of the present invention.

BRIEF DESCRIPTION OF THE DRAWING

FIG. 1 is a graph showing the effects of adding copper sulfate to co-culture media on the transient expression of the GUS gene in maize (A188). The ordinate indicates quantification of the area of spots showing the transient expression of the GUS gene in the range from 0 (no expression) to 4 (expression on nearly the entire surface of the scutellum). "Cu x" (where x represents a number) shown on the abscissa of the graph means that the concentration of copper sulfate in the co-culture medium is x μM.

FIG. 2 is a graph showing the effects of concentration of copper sulfate in co-culture media on callus formation in maize (H99) after co-culture. On the abscissa of the graph, "Ag x" and "Cu x" (where x represents a number) mean that the concentrations of silver nitrate and copper sulfate in the co-culture medium are x μM, respectively.

FIG. 3 is a graph showing the effects of concentration of copper sulfate in co-culture media on phosphinothricin (PPT)-resistant callus formation in maize (A188) after co-culture. The ordinate indicates quantification of callus formation at levels from 0 (no callus formed) to 3 (the entire scutellum formed callus). "Cu x" (where x represents a number) shown on the abscissa of the graph means that the concentration of copper sulfate in the co-culture medium is x μM.

FIG. 4 is a graph showing the effects of adding copper sulfate to a coculture medium on the transient expression of the GUS gene in rice (IR64). The ordinate indicates quantification of the area of spots showing the transient expression of the GUS gene in the range from 0 (no expression) to 4 (expression on nearly the entire surface of the scutellum). "Cu 5" shown on the abscissa of the graph means that the concentration of copper sulfate in the co-culture medium is 5 μM.

FIG. 5 is a graph showing the effects of adding copper gluconate to a co-culture media on the transient expression of the GUS gene in maize (A188). The ordinate indicates quantification of the area of spots showing the transient expression of the GUS gene in the range from 0 (no expression) to 4 (expression on nearly the entire surface of the scutellum).

FIG. 6 is a graph showing the effects of adding copper gluconate to co-culture media on callus formation in maize (A188). The ordinate indicates quantification of callus formation at levels from 0 (no callus formed) to 3 (the entire scutellum formed callus).

FIG. 7 is a graph showing the effects of adding copper sulfate or copper gluconate to co-culture media on the growth of immature embryos of rice (Yukihikari). The ordinate indicates the average weight of immature embryos which formed callus, per immature embryo. On the abscissa, Experiments 1, 2, 3 represent experiments independently performed; cont. represents a control lacking copper sulfate or copper gluconate; Cu represents copper sulfate; and CG represents copper gluconate. The numerical values following Cu and CG represent their concentrations (μM) in the coculture medium.

FIG. 8 is a graph showing the effects of adding copper sulfate or copper gluconate to regeneration media on the growth of transformed plants regenerated from maize (A188)

transformed calli. The ordinate indicates the average of the leaf length of regenerated plants. On the abscissa, cont. represents a control lacking copper sulfate or copper gluconate; Cu represents copper sulfate; and CG represents copper gluconate. Copper sulfate and copper gluconate were added at 10 µFM to their co-culture media.

FIG. 9 is a graph showing the effects of adding copper sulfate or copper gluconate to regeneration media on the growth of transformed plants regenerated from rice (Yukihikari) transformed calli. The ordinate indicates the average of the leaf length of regenerated plants. On the abscissa, cont. represents a control lacking copper sulfate or copper gluconate; Cu represents copper sulfate; and CG represents copper gluconate. Copper sulfate and copper gluconate were added at 10 µM to their co-culture media.

EXAMPLES

Example 1

Effects of Adding Copper Sulfate to Co-culture Media on Maize Transformation

Materials and Methods

Immature embryos (size: 1.0-1.5 mm) of maize (cultivars: A188, H99) at days 7-14 post-pollination were aseptically collected and washed once in LS-inf liquid medium (LS salts, 0.5 mg/l nicotinic acid, 0.5 mg/l pyridoxine hydrochloride, 1 mg/l thiamine hydrochloride, 100 mg/l myoinositol, 1 g/l casamino acids, 1.5 mg/l 2,4-D, 68.5 g/l sucrose, 36 g/l glucose, pH 5.2; see Ishida, Y., et al., (1996), Nature Biotechnology, Vol. 4, p. 745-750). The immature embryos were partially pretreated for increasing the gene transduction efficiency (heated at 46° C. for 3 minutes and centrifuged at 15,000 rpm for 10 minutes). *Agrobacterium tumefaciens* LBA4404 (pSB131) (carrying a PPT (phosphinothricin) resistance gene driven by the cauliflower mosaic virus 35S promoter and the GUS gene containing a castor bean catalase intron fused to the cauliflower mosaic virus 35S promoter in the T-DNA region; see Ishida, Y., et al., (1996), Nature Biotechnology, Vol. 4, p. 745-750) was suspended at about 1.0× $10^9$ cfu/ml in LS-inf liquid medium containing 100 µM acetosyringone to prepare an inoculum. The inoculum was added to the collected/washed immature embryos and heated/centrifuged immature embryos, and the suspensions were agitated for 30 seconds and then allowed to stand for 5 minutes at room temperature. The *Agrobacterium*-inoculated immature embryos were plated on co-culture media containing $CuSO_4.5H_2O$ at a concentration of 0-10 µM in LS-AS medium containing 5 µM $AgNO_3$ (LS salts, 0.5 mg/l nicotinic acid, 0.5 mg/l pyridoxine hydrochloride, 1 mg/l thiamine hydrochloride, 100 mg/l myoinositol, 700 mg/l L-proline, 1.5 mg/l 2,4-D, 20 g/l sucrose, 10 g/l glucose, 500 mg/l MES, 100 µM acetosyringone, 8 g/l agar, pH 5.8; see Ishida, Y., et al., (1996), Nature Biotechnology, Vol. 4, p. 745-750, in which 8 g/l agarose is used as a gelling agent) with the embryonic disc facing upward.

The immature embryos were incubated at 25° C. in darkness for 3 days and then partially immersed in a 0.1 M phosphate buffer (pH 6.8) containing 0.1% Triton X-100, and allowed to stand at 37° C. for 1 hour. After *Agrobacterium* was removed with the phosphate buffer, a phosphate buffer containing 1.0 mM 5-bromo-4-chloro-3-indolyl-β-D-glucuronic acid (X-gluc) and 20% methanol was added. The immature embryos were treated at 37° C. for 24 hours, and then observed under a microscope to assess the area of blue-stained tissue.

The immature embryos incubated on co-culture media for 3 days were plated on LSD 1.5 medium (LS salts, 0.5 mg/l nicotinic acid, 0.5 mg/l pyridoxine hydrochloride, 1 mg/l thiamine hydrochloride, 100 mg/l myoinositol, 700 mg/l L-proline, 1.5 mg/l 2,4-D, 20 g/l sucrose, 500 mg/l MES, 8 g/l agar, pH 5.8; see Ishida, Y., et al., (1996), Nature Biotechnology, Vol. 4, p. 745-750) and incubated at 25° C. in darkness for about 4 weeks, and then measured for the diameters of grown calli. The immature embryos incubated on co-culture media for 7 days were seeded on LSD 1.5 medium containing 5 mg/l phosphinothricin (PPT) and incubated at 25° C. in darkness for 1 week, and then observed under a microscope to assess the extent of callus formation. These calli were cultured on the same medium containing 10 mg/l PPT for 6 weeks under the same conditions. Grown PPT-resistant calli were seeded on LSZ regeneration medium (LSD 1.5 medium deprived of 2,4-D and supplemented with 5 mg/l zeatin) and incubated at 25° C. under illumination for 2-3 weeks. Leaf segments of regenerated plants were excised and assessed for the expression of the GUS gene by X-gluc.

Results

Immature embryos (cultivar: A188) incubated on various coculture media for 3 days were stained with X-gluc, and the area of spots showing the transient expression of the GUS gene (blue spots) was evaluated on a scale of five ratings from 0 (no expression) to 4 (expression on nearly the entire surface of the scutellum).

Immature embryos incubated on co-culture media containing 1, 5 and 10 µM copper sulfate for 3 days showed the transient expression of the GUS gene in a wider area of the scutellum as compared with immature embryos incubated on a control medium. The increase of the area showing the transient expression of the GUS gene by adding copper sulfate to co-culture media was observed irrespective of whether or not heat/centrifugation pretreatment was performed (FIG. 1). These results showed that the gene introduction efficiency increases by adding copper sulfate to co-culture media.

Immature embryos (cultivar: H99) incubated on various co-culture media for 3 days were cultured on a medium containing no selective pressure for about 4 weeks, and then measured for the diameters of formed calli. Immature embryos incubated on a co-culture medium containing 5 µM silver nitrate showed callus growth nearly comparable to that of immature embryos cultured on a control medium. In contrast, immature embryos incubated on a co-culture medium containing 10 µM copper sulfate and 5 µM silver nitrate had an average diameter greater than that of immature embryos incubated on a control co-culture medium by 2 mm or more, showing that addition of copper sulfate promotes callus growth (FIG. 2).

After co-culture for 1 week, the calli grown from immature embryos (cultivar: A188) cultured on a selective medium containing PPT for 1 week were evaluated on a scale of four ratings from 0 (no callus formed) to 3 (the entire scutellum formed callus). Immature embryos cultured on media containing copper sulfate showed higher callus formation as compared with immature embryos cultured on a control medium, showing that addition of copper sulfate improves the efficiency of transformed callus formation (FIG. 3). Further selection on a medium containing PPT and incubation of the resulting calli in a regeneration medium containing PPT gave PPT-resistant plants. Leaf segments of these plants were excised and assessed for the expression of the GUS gene. As a result, immature embryos incubated on co-culture media containing 5 and 10 µM copper sulfate showed a 2- to 3-fold higher transformation efficiency than that of immature embryos incubated on a co-culture medium lacking copper sulfate (Table 1).

TABLE 1

Effects of adding copper sulfate to co-culture media on transformation efficiency

| CuSO$_4$ (μM) | Number of inoculated immature embryos (A) | Number of regenerated plants | Number of GUS-positive plants (B) | Transformation efficiency (B/A, %) |
|---|---|---|---|---|
| 0 | 13 | 2 | 2 | 15.4 |
| 1 | 13 | 2 | 2 | 15.4 |
| 5 | 13 | 6 | 6 | 46.2 |
| 10 | 14 | 6 | 5 | 35.7 |

Thus, it was shown that addition of copper sulfate to co-culture media has the effect of increasing *Agrobacterium*-mediated gene introduction efficiency, promoting callus formation and growth, and improving transformation efficiency.

Example 2

Effects of Adding Copper Sulfate to Co-Culture Media on Gene Introduction of Rice Materials and Methods An *Agrobacterium tumefaciens* super-binary vector designated LBA4404 (pSB134) (carrying the HPT gene (hygromycin resistance gene) fused to a ubiquitin intron driven by a maize ubiquitin promoter and the GUS gene fused to a castor bean catalase intron driven by the cauliflower mosaic virus 35S promoter in the T-DNA region; construction of pSB134 was performed by inserting a 35S-intron GUS-nos fragment derived from pSB32 as an expression marker into HindIII of pKY205 (see WO 03/027290)) cultured on AB medium (3 g/l KH$_2$PO$_4$, 1 g/l NaH$_2$PO$_4$, 1 g/l NH$_4$Cl, 300 mg/l MgSO$_4$.7H$_2$O, 150 mg/l KCl, 10 mg/l CaCl$_2$, 2.5 mg/l FeSO$_4$.7H$_2$O, 5 g/l glucose, 15 g/l agar, pH 7.0; Chilton, M.-D., et al., (1974), Proc. Natl. Acad. Sci. U.S.A., 71:3672-3676) containing 50 mg/l hygromycin and 50 mg/l spectinomycin for 3 to 4 days was scraped with a platinum loop and suspended at a concentration of about $10^9$ cfu/ml in 1 ml of AA1 liquid medium (AA major salts, LS minor salts, MS vitamins, AA amino acids, 0.2 g/l casamino acids, 4 g/l sucrose, 2 g/l glucose, pH 5.2) containing 100 μM acetosyringone. Into an Eppendorf tube containing aseptically collected immature embryos (cultivar: IR64) was added 1 ml of the *Agrobacterium* suspension and the tube was agitated for 30 seconds in a vortex mixer and then allowed to stand at room temperature for 5 minutes. The immature embryos were plated on nN6-As medium (N6 salts, N6 vitamins, 0.5 g/l casamino acids, 0.5 g/l L-proline, 1 mg/l 2,4-D, 0.5 mg/l NAA, 0.1 mg/l 6BA, 20 g/l sucrose, 10 g/l glucose, 10 μM AgNO$_3$, 100 μM acetosyringone, 8 g/l agarose, pH 5.2) and nN6-As medium containing 5 μM CuSO$_4$.5H$_2$O and incubated in darkness at 25° C. for one week.

Results

Co-cultured immature embryos were stained with X-gluc, and the area of spots showing the transient expression of the GUS gene (blue spots) was evaluated on a scale of five ratings from 0 (no expression) to 4 (expression on nearly the entire surface of the scutellum).

Immature embryos incubated on a co-culture medium containing 5 μM copper sulfate for 1 week showed the transient expression of the GUS gene in a wider area of the scutellum as compared with immature embryos cultured on a control medium (FIG. 4). This showed that the improvement in gene introduction efficiency by adding copper sulfate to co-culture media is found in not only maize but also rice.

Example 3

Effects of Adding Copper Gluconate to Co-Culture Media on Gene Introduction of Maize Materials and Methods Immature embryos (size: 1.0-1.5 mm) of maize (cultivar: A188) at days 7-14 post-pollination were aseptically collected and washed once in LS-inf liquid medium. A pretreatment for increasing gene transduction efficiency (heating at 46° C. for 3 minutes and centrifugation at 15,000 rpm for 10 minutes) was performed. *Agrobacterium tumefaciens* LBA4404 (pSB131) was suspended at about $1.0 \times 10^9$ cfu/ml in LS-inf liquid medium containing 100 μM acetosyringone to prepare an inoculum. The inoculum was added to the heated/centrifuged immature embryos, and the suspension was agitated for 30 seconds and then allowed to stand for 5 minutes at room temperature. The *Agrobacterium*-inoculated immature embryos were plated on co-culture media containing copper gluconate at a concentration of 0-10 μM in LS-AS medium containing 5 μM AgNO$_3$ with the scutellum facing upward.

The immature embryos were incubated at 25° C. in darkness for 3 days and then partially immersed in a 0.1 M phosphate buffer (pH 6.8) containing 0.1% Triton X-100, and allowed to stand at 37° C. for 1 hour. After *Agrobacterium* was removed with the phosphate buffer, a phosphate buffer containing 1.0 mM 5-bromo-4-chloro-3-indolyl-β-D-glucuronic acid (X-gluc) and 20% methanol was added. The immature embryos were treated at 37° C. for 24 hours, and then observed under a microscope to assess the area of blue-stained tissue.

The immature embryos incubated on co-culture media for 7 days were evaluated for callus formation on a scale of ratings 0 (no callus formed), 1 (a part of the scutellum formed callus), 2 (about a half of the scutellum formed callus), and 3 (¾ or more of the scutellum formed callus).

Results

Immature embryos (cultivar: A188) incubated on various co-culture media for 3 days were stained with X-gluc, and the area of spots showing the transient expression of the GUS gene (blue spots) was evaluated on a scale of five ratings from 0 (no expression) to 4 (expression on nearly the entire surface of the scutellum). Immature embryos incubated on co-culture media containing 1, 5 and 10 μFM copper gluconate for 3 days showed the transient expression of the GUS gene in a wider area of the scutellum as compared with immature embryos cultured on a control medium (FIG. 5).

Immature embryos incubated on co-culture media for 1 week was assessed for callus formation. All immature embryos incubated on co-culture media containing 1, 5 and 10 μM copper gluconate showed higher callus formation than that of immature embryos co-cultured on a medium lacking copper gluconate. Especially, significantly higher callus formation was shown on co-culture media containing 5 and 10 μM copper gluconate as compared with control (FIG. 6).

These results showed that gene introduction efficiency and callus formation efficiency increase by adding copper gluconate to co-culture media in the same manner that copper sulfate is added.

Example 4

Effects of Adding Copper Sulfate and Copper Gluconate to Inoculum Liquid Media on Gene Introduction of Rice Materials and Methods An *Agrobacterium tumefaciens* super-binary vector designated LBA4404 (pSB134) cultured on AB medium containing 50 mg/l hygromycin and 50 mg/l spectinomycin for 3 to 4 days was scraped with a platinum loop and suspended at a concentration of about $10^9$ cfu/ml in 1 ml of AA1 liquid medium containing 100 μM acetosyringone and 0-50 μM $CuSO_4.5H_2O$ or copper gluconate. Into an Eppendorf tube containing aseptically collected immature embryos (cultivar: Yukihikari) was added 1 ml of the *Agrobacterium* suspension and the tube was agitated for 30 seconds in a vortex mixer and then allowed to stand at room temperature for 5 minutes. The immature embryos were seeded on nN6-As medium and incubated in darkness at 25° C. for one week.

Results

The weight of co-cultured immature embryos was measured. In all three experiments, immature embryos cultured on inoculum liquid media containing copper sulfate or copper gluconate showed more active growth than immature embryos cultured on a control medium lacking copper sulfate or copper gluconate (FIG. 7). This showed that the improvement in callus growth by adding copper sulfate and copper gluconate is equally observed not only when they are added to co-culture media but also when they are added to inoculum liquid media.

Example 5

Effects of Adding Copper Sulfate, Copper Gluconate to Regeneration Media on the Growth of Transformed Maize Plants Materials and Methods Immature embryos (size: 1.0-1.5 mm) of maize (cultivar: A188) were inoculated with *Agrobacterium tumefaciens* LBA4404 (pSB131) and cultured on LSD 1.5 medium containing PPT to give a transformed callus. The transformed callus was cut into a size of about 2 mm and plated on LSZ regeneration medium containing 10 μM $CuSO_4.5H_2O$ or copper gluconate, and PPT. After incubation at 25° C. under illumination for 3 weeks, the leaf length of regenerated plants was measured.

Results

The leaf length of plants regenerated on a regeneration medium containing copper sulfate or copper gluconate was significantly longer than that of plants regenerated on a control regeneration medium, showing that copper sulfate or copper gluconate has the effect of promoting the growth of regenerated plants (FIG. 8).

Example 6

Effects of Adding Copper Sulfate, Copper Gluconate to Regeneration Media on the Growth of Transformed Rice Plants Materials and Methods Immature embryos of rice (cultivar: Yukihikari) were inoculated with *Agrobacterium tumefaciens* LBA4404 (pSB134) and cultured on nN6CC medium (N6 salts, N6 vitamins, 0.5 g/l casamino acids, 0.5 g/l L-proline, 1 mg/l 2,4-D, 0.5 mg/l NAA, 0.1 mg/l 6BA, 20 g/l sucrose, 55 g/l sorbitol, 250 mg/l cefotaxime, 250 mg/l carbenicillin, 5 g/l Gelrite, pH 5.8) containing hygromycin to give a transformed callus. The transformed callus was cut into a size of about 2 mm and seeded on N6R regeneration medium (N6 salts with major salts reduced to ½, N6 vitamins, AA amino acids, 1 g/l casamino acids, 0.5 mg/l kinetin, 20 g/l sucrose, 30 g/l sorbitol, 4 g/l Gelrite, pH 5.8) containing 10 μM $CuSO_4.5H_2O$ or copper gluconate, and hygromycin. After incubation at 25° C. under illumination for 3 weeks, the leaf length of regenerated plants was measured.

Results

The leaf length of plants regenerated on a regeneration medium containing copper sulfate or copper gluconate was significantly longer than that of plants regenerated on a control regeneration medium, whereby it was also shown in rice that copper sulfate or copper gluconate has the effect of promoting the growth of regenerated plants (FIG. 9).

INDUSTRIAL APPLICABILITY

The present invention provides inexpensive and convenient gene introduction methods with higher efficiency than conventional *Agrobacterium*-mediated methods. It also provides methods that can be adapted to plant species and cultivars involving difficulty in gene introduction by conventional *Agrobacterium*-mediated methods. The methods of the present invention improve gene introduction efficiency and/or transformation efficiency and/or promote the growth of regenerated plants as compared with cases where a medium containing a metal salt at a normal level is used.

As shown in FIG. 1, the gene introduction efficiency in a monocotyledon maize was improved to a 2-fold to 2.5-fold higher level by using co-culture media containing copper sulfate at high concentrations as compared with the case where a medium lacking copper sulfate was used. The gene introduction efficiency was further improved to a 1.5-fold to 3-fold higher level by heating/centrifugation as compared with the case where a medium lacking copper sulfate and untreated plant materials were used.

The present invention improved *Agrobacterium*-mediated gene introduction efficiency in plants, thereby allowing many transformed plants to be efficiently obtained, contributing to efficient and easy culture of cultivars containing a practical gene. Especially, the improvement in transformation efficiency by the methods of the present invention is very significant because the transformation efficiency of monocotyledons, especially maize by conventional *Agrobacterium*-mediated methods is low.

The invention claimed is:

1. A method for *Agrobacterium*-mediated gene transduction into a plant material, comprising:
   1) preparing the plant material, and then
   2) infecting the plant material with an *Agrobacterium*,
characterized in that a medium enriched in a metal salt containing copper ion is used at least in step 2), wherein said plant material is an immature monocotyledonous embryo or a callus of a monocotyledonous plant.

2. The method of claim 1, wherein the metal salt is copper sulfate or copper gluconate.

3. The method of claim 1, wherein the metal salt is copper sulfate.

4. The method of claim 1, wherein a medium enriched in copper sulfate or copper gluconate is used in at least step 2) of infecting the plant material with an *Agrobacterium*.

5. The method of claim 1, wherein a medium containing 1-50 μM copper sulfate or copper gluconate is used in at least step 2) of infecting the plant material with an *Agrobacterium*.

6. The method of claim 1, further comprising subjecting the plant material to at least one treatment selected from the group consisting of pressurization, heat treatment, centrifugation and sonication in step 1) of preparing the plant material and/or step 2) of infecting the plant material with an *Agrobacterium*.

7. The method of claim 1, wherein the monocotyledonous plant is maize.

8. The method of claim 1, wherein the monocotyledonous plant is rice.

9. The method of claim 1, wherein the plant material is an immature monocotyledonous embryo.

10. The method of claim 1, further comprising the steps of:
    3) selecting a transformed cell, and
    4) optionally regenerating the selected transformant, subsequently to step 2) of infecting the plant material with an *Agrobacterium*.

11. The method of claim 1, further comprising the steps of:
    3) selecting a transformed cell, and
    4) optionally regenerating the selected transformant, subsequently to step 2) of infecting the plant material with an *Agrobacterium*, wherein a medium enriched in a metal salt containing copper ion is used in at least one of the steps above.

12. A process for preparing a transformed plant characterized in that the method of claims 10 or 11 is used.

13. The method of claim 1, wherein the medium containing 1-10 μM copper sulfate or copper gluconate is used in at least step 2) of infecting the plant material with an *Agrobacterium*.

14. A method for *Agrobacterium*-mediated gene transduction into a plant material, comprising:
    1) preparing the plant material, and then
    2) infecting the plant material with an *Agrobacterium*,
    3) selecting a transformed cell, and
    4) regenerating the selected transformant, characterized in that a medium enriched in a metal salt containing a copper ion is used in steps 2) and 4), wherein said plant material is an immature monocotyledonous embryo or a callus of a monocotyledonous plant.

15. A method for *Agrobacterium*-mediated gene transduction into a plant material, comprising:
    1) preparing the plant material, and then
    2) infecting the plant material with an *Agrobacterium*,
    3) selecting a transformed cell, and
    4) regenerating the selected transformant, characterized in that a medium enriched in a metal salt containing copper ion is used in step 2), wherein said plant material is an immature monocotyledonous embryo or a callus of a monocotyledonous plant.

* * * * *